(12) United States Patent
Striker et al.

(10) Patent No.: US 6,214,542 B1
(45) Date of Patent: Apr. 10, 2001

(54) QUANTIFICATION OF INDICATORS OF FIBROSIS

(75) Inventors: Gary E. Striker; Liliane J. Striker; Emmanuel Peten, all of Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 07/963,475

(22) Filed: Oct. 20, 1992

(51) Int. Cl.$^7$ ........................................... C12Q 1/68
(52) U.S. Cl. ............................ 435/6; 435/91.2
(58) Field of Search ................... 435/6, 91, 91.2

(56) References Cited

FOREIGN PATENT DOCUMENTS 0 461 496    12/1991    (EP) .

OTHER PUBLICATIONS

Peten et al. "Quantitation of α1 Type IV mRNA in Single Glomeruli of Glomerulosclerotic Mice . . . ", *J.Am.Soc. Nephrology* 2(3):581 (1991).

Peten et al. "Isolated Single Mouse Glomeruli Express Type IV But Not TYPE I Collagen mRNA", *J. Am. Soc. Nephrology* 3(2):580 (1991).

Carome et al. "TIMP1 and α1 Type IV Collagen mRNAs in Mouse Mesangial Cells at Low and High Density", *J. Am. Soc. Nephrology* 2(3):572 (1991).

Doi et al. "Glomerulosclerosis in Mice Transgenic for Growth Hormone. Increased Mesangial Extracellular Matrix . . . ", *J. Exp. Medicine* 173:1287–1290 (1991).

Merritt et al. "Analysis of α1 (I) Procollagen α1(IV) Collagen, and β–actin mRNA in Glomerulus . . . ", *Laboratory Investigation* 63(6):762–769 (1990).

M.M. Striker et al. "The Composition of Glomerulosclerosis", *Laboratory Investigation* 51(2):181–192 (1984).

Pesce et al. "Glomerulosclerosis at Both Early and Late Stages Is Associated with Increased Cell Turnover . . . ", *Laboratory Investigation* 65(5):601–605 (1991).

Moriyama et al. "Detection of Specific mRNAs in Signel Nephron Segments by Use of the Polymerase Chain Reaction", *Am. J. Physiol.* 258(5):F1470–F1474 (1990).

Gilliland et al. "Analysis of Cytokine mRNA and DNA: Detection and Quantitation by Competitive Polymerase . . . ", *Proc. Natl. Acad. Sci.* 87(7):2725–2729 (1990).

Cao et al, "Identification and Quantitation of HIV–1 in the Liver of Patients With AIDS," *AIDS*, 6:65–70 (1992).

*Primary Examiner*—Scott W. Houtteman
(74) *Attorney, Agent, or Firm*—David Sadowski

(57) ABSTRACT

The state of the extracellular matrix of discrete tissue subsegments can be determined via an approach that combines microdissection, reverse transcription and polymerase chain reaction. Using this approach, a positive correlation between a fibrotic condition and alterations in messenger RNA levels of matrix components provides the basis for (i) the diagnosis of a fibrotic disease and (ii) the monitoring of the efficacy of a therapeutic regimen.

16 Claims, 1 Drawing Sheet

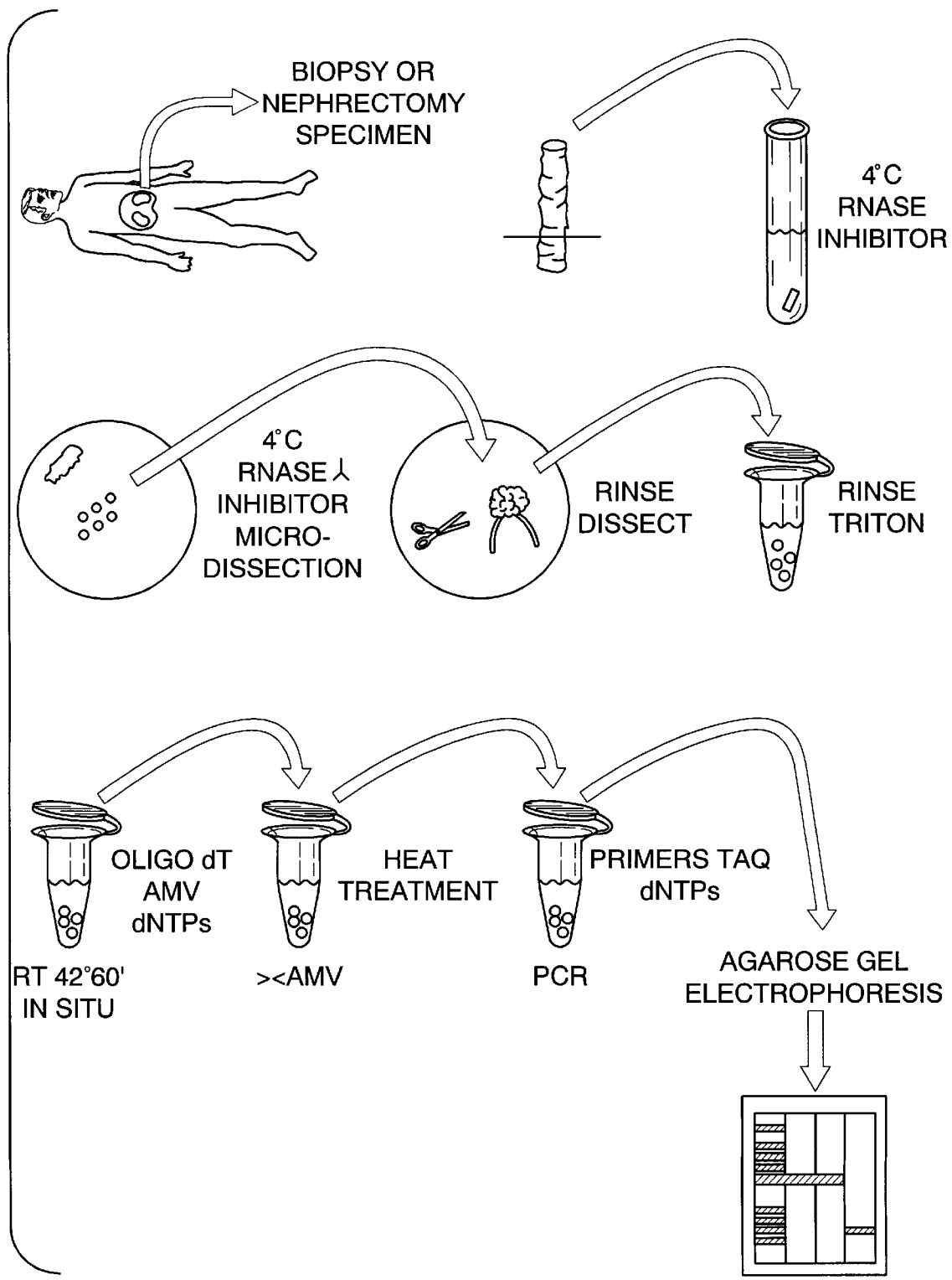

QUANTIFICATION OF INDICATORS OF FIBROSIS

BACKGROUND OF THE INVENTION

Fibrosing diseases are known to affect many different mammalian organs. Common examples include the kidney (glomerulonephritis), bladder, prostate (benign prostate hypertrophy), lung (emphysema) and liver. But essentially all tissues are affected, in one way or another, by the fibrotic process. This is due mainly to the wide range of different cells types, such as fibroblasts, smooth muscle cells, and even epithelial cells, that are involved in fibrotic disease. The common thread that links all these cells types with fibrotic disease is the synthesis of connective tissue.

Until recently, it was believed that fibrosis was a terminal and irreversible process consisting of the deposition of intert connective tissue in the scarring process. It is now thought that fibrosis is a dynamic process up to the end stages of disease. In other words, deposition of scar tissue continues until the affected tissue is almost completely replaced by scar tissue. This finding has considerable therapeutic import since even a fairly late diagnosis of the disease may permit an effective implementation of therapy. It remains quite important to make an accurate diagnosis as early as possible, however, in order to minimize the damage to affected tissues. Unfortunately, overt clinical signs of disease, usually marked by the beginning of organ failure, often do not occur until more than one-half of the organ has been scarred.

One of the devastating manifestations of fibrotic disease is kidney failure. In fact, the most common cause of end-stage renal disease in humans is the result of gradual, glomerular scarring known as glomerulosclerosis. United States Renal Data System, National Institute of Diabetes, Digestive and Kidney Diseases, National Institutes of Health, 1991. The glomerulus is a tuft of capillaries situated at the origin of the vertebrate kidney that is responsible for filtering impurities from the blood, resulting in the formation of urine. A major cause of glomerular scarring is fibrosis resulting from the excessive deposition of extracellular matrix (ECM) components in the glomerular region. Presumably, this deposition results from a deviation in the tightly regulated balance between the synthesis and degradation of the molecules which comprise the ECM. Little is known concerning the molecular basis of this abnormality.

The ECM is a complex network of macromolecules that fills the tissue space between cells. Until recently, it was thought that the ECM provided a relatively inert scaffold on which cells found support. But it is now clear that this structure is intimately involved with the development and function of many cell types.

The ECM of vertebrates is made up of two general groups of molecules, glycosaminoglycans (GAG's) and fibrous proteins. GAG's are long polymers of repeating disaccharide units, most of which are covalently linked to protein molecules to form proteoglycans. The fibrous proteins are of two classes, adhesive and structural. The major fibrous protein, collagen, is of the latter type.

There are at least ten different collagens presently known, all comprised of trimeric helices. The individual protein subunits that comprise the helix are characterized by a repeating "gly-X-Y" unit, where X and Y can be any amino acid, but are often proline. The small glycine residue allows for tight winding of the three subunits into a triple $\alpha$-helix structure. The best characterized proteins of this family of molecules are collagens I–IV. Type II collagen and type III collagen are each composed of three identical subunits, $\alpha 1$(II) and $\alpha 1$(III) respectively. Type I collagen is comprised of two $\alpha 1$(I) subunits and one $\alpha 2$(I) subunit. Likewise, type IV collagen is comprised of two $\alpha 1$(IV) subunits and one $\alpha 2$(IV) subunit. Depending on the tissue type, the collagen make up of the ECM can differ dramatically and individual collagens may be further modified depending on their location and role.

Type IV collagen has been shown to be the major component of the glomerulosclerotic lesion. Morel-Maroger Striker et al., *Lab. Invest.* 51:181–192 (1984). Type I collagen, which is not normally found in the glomerular ECM, has also been identified by immunofluorescence in the sclerotic lesion. Merritt et al., *Lab. Invest.* 63:762–769, 1990. In addition, there is evidence linking most other kinds of collagen with the generation of scar tissue. Id.

Yet another group of molecules which contribute to the extracellular matrix system, and potentially to fibrotic disease, is the metalloproteinase family. These enzymes mediate matrix degradation by type-specific cleavage of collagens. Liotta, L. A. and W. G. Stetler-Stevenson, *Sem. Can. Bio.* 1:99–106 (1990); Woessner, J. F., *FASEB J.* 5:2145–2154 (1991). For example, interstitial collagenases cleave type I and type III collagen, whereas 66–72 and 92 kDa gelatinases degrade non-helical type IV and V collagens as well as denatured interstitial collagenases. The action of these enzymes is modulated by a family of tissue inhibitors of metalloproteinases, or TIMP's, two of which, TIMP-1 and TIMP-2, have been characterized in certain cells and tissues from humans. Carmichael et al., *Proc. Nat'l Acad. Sci.* 83:2407–2411 (1986); Stetler-Stevenson et al., *J. Biol. Chem.* 264:17374–17378 (1989). These inhibitors inactivate all matrix metalloproteinases through formation of an enzyme-inhibitor complex exhibiting a 1:1 stoichiometry. Mesangial cells, one of the three major cell types in the glomerulus, synthesize both TIMP-1 and TIMP-2, as well as a variety of metalloproteinases. Martin et al., *J. Immunol.* 137:525–529 (1986); Kawanishi, et al., *J. Am. Soc. Nephrol.* 2:577 (1991).

The overall gross pathology of fibrotic disease is characterized by an increase in tissue rigidity, a concomittant loss of elasticity, and eventual replacement of organ tissue with scar. Such alterations also adversely affect the function of the organ. The specific cellular changes that occur are presently the subject of intense investigation. What can be said is that the deposition of excess ECM, which leads to scar formation, causes substantial changes in the behavior of cells. The reasons for the production and deposition of excess ECM remain largely unknown.

Unfortunately, the study of the phenomena discussed above has been hampered for a number of reasons. Glomeruli represent only a small fraction of the kidney, thus making studies of whole kidney, or even cortex, difficult to relate to glomerlular change. In addition, it has not been possible to obtain sufficient quantities of such tissues from human subjects in order to do meaningful research. Also, glomeruli appear to be regulated independently of other kidney tissue, making studies of whole kidneys difficult to relate to these specific renal tissues. Doi et al., *Am. J. Pathol.* 131:398–403 (1988); Pesce et al., *Lab. Invest.* 65:601–605 (1991). Study of collagen synthesis is further slowed by low levels of messenger RNA's corresponding to these proteins. Laurie et al., *J. Cell Biol.* 109:1351–1362 (1989). And finally, while glomerular cells can be propagated in vitro, such studies cannot be readily extrapolated to the intact structure since phenotypic changes in matrix metabolism occur in cell culture. Striker et al., *Transplant. Proc.* 12:88–99 (1980); Morel-Maroger Striker et al., *Lab. Invest.*

51:181–192 (1984). As a general matter, these difficulties are characteristic of the study of fibrotic disease in other tissues as well.

The foregoing serves to highlight the lack of adequate diagnostic capability with respect to glomerular fibrosis. Without a simple and effective way to detect early fibrotic changes, there is little hope that treatment can be implemented soon enough to avoid tissue damage and possible organ failure.

SUMMARY OF THE INVENTION

It is therefore an object of the present invention to provide a method by which the state of the extracellular matrix environment can be determined, at the molecular level, in order to make an early diagnosis of a fibrosing condition.

It is a further object of the present invention to provide a method by which the state of the extracellular matrix environment of a given tissue can be monitored, over the course of time in a single patient, in order to evaluate disease progression.

Another object of the present invention is to provide a method by which the state of the extracellular matrix environment of a given tissue can be monitored, over the course of time in a single patient, in order to determine the effectiveness of a course of treatment.

In satisfying the foregoing objects, there has been provided, in accordance with one aspect of the present invention, a diagnostic method comprising the steps of (i) obtaining a sample of tissue from an organism by biopsy, wherein said tissue is subject to a fibrosing condition;

then (ii) isolating by microdissection an intact subsegment of said sample, which subsegment corresponds to a basic organizational structure of said tissue;

(iii) subjecting mRNA from said subsegment to reverse transcription to obtain cDNA molecules;

and thereafter (iv) bringing said cDNA molecules into contact with PCR primers under conditions such that a subpopulation of said cDNA molecules undergoes amplification, wherein cDNAs of said subpopulation encode protein molecules that are involved in basement membrane-synthetic and -degradative pathways related to said fibrosing condition.

In preferred embodiments, the amount of amplified cDNA molecules is compared with that of a second organism or, alternatively, of the same organism but generated at an earlier time. In another preferred embodiment, the obtained tissue is kidney tissue.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 is a schematic representation of one aspect of the present invention, including the steps of biopsy, microdissection, reverse transcription, cDNA amplification, and analysis of the amplified products.

DETAILED DESCRIPTION OF PREFERRED EMBODIMENTS

It has been discovered that the progression of the scarring which is a hallmark of fibrotic disease can be followed, and a counteracting therapeutic regimen implemented, by reference to mRNA levels monitored in a functionally discrete portion (subsegment) of the affected organ. By combining microdissection with powerful molecular techniques, namely, reverse transcription and quantitative PCR, the present invention also overcomes obstacles encountered heretofore in the diagnosis of fibrotic disease. As a result, it is possible to implement treatment sooner, thereby preventing significant damage to susceptible tissues.

In particular, the present invention permits one to detect even subtle changes in the nature of the extracellular matrix. The mRNA levels corresponding to certain ECM proteins are often seen to increase in sclerotic regions and appear to be independent of cell number. And there is a positive correlation between histologic findings of sclerosis and the amount of certain ECM-related mRNA's.

The present invention employs a series of steps through which discrete regions of organ tissue are examined for abnormalities in extracellular matrix synthesis and degradation. These steps include tissue biopsy, microdissection, reverse transcription, and polymerase chain reaction (PCR). The net result of the combination of these steps is two-fold. First, biopsy and microdissection serve to parse out particular tissues for study. And second, reverse transcription and PCR serve to amplify molecules available only in trace amounts in the dissected tissues, thus allowing for their study ex vivo.

The present invention may be applied to the study of fibrosis in almost any tissue. Since all tissues contain connective tissue, there will be some cells responsible for the deposition of connective tissue components (e.g., collagens) in each location. Thus, the potential for abnormal scar formation exists and can be studied employing the methods claimed herein.

Current technology used to study renal fibrosis requires large amounts of tissue. Fogel et al., *Am. J. Pathol.* 138:465–475 (1991); Merritt et al. (1990); Nakamura et al., *Lab. Invest.* 64:640–647 (1991). As noted above, it has been difficult, due to technical limitations, to generate sufficient quantities of tissue from living organisms. The present invention circumvents these problems by using biopsy and microdissection. Biopsy is simply the removal of a small sample of intact tissue for diagnostic, as opposed to therapeutic purposes. In this context, biopsy of tissue allows one to look at tissue that has developed in its normal environment and that was not subject to the effects of manipulations outside the organism. Biopsy also can be performed such that the organism to be studied need not be sacrificed. In fact, most biopsies can be performed percutaneously with a biopsy needle and the assistance of imaging techniques. Thus, discomfort to the patient and damage to the organ are minimized.

While biopsies can target specific parts of the organism for study, it is often desirable to examine even smaller segments of the tissue, especially when the effects of disease are localized to these areas. This is accomplished by further subjecting the isolated tissue to microdissection. "Microdissection" is defined as the isolation of small samples of organ tissue in order to facilitate the study of particular subsegments of that organ. The dissected subsegments should provide the basic organizational units of such tissues and remain essentially intact following microdissection in order to allow results to be correlated with subsegment function. In each tissue there are usually a number of distinct subsegments with differing functions. By examining a discrete subsegment, one can focus attention on a particular function or set of functions associated therewith. A general description of microdissection can be found in Moriyama et al., *Am. J. Physiol.* 258:F1470–F1474 (1990). Microdissection also provides a further advantage in that the use of such small samples minimizes the negative effects on the subject.

Thus, the coupling of biopsy and microsdissection avoids many of the difficulties associated with prior technology. It also, unfortunately, means that only small quantities of tissue are available on which to conduct research. This is further compounded when one wishes to examine disease at the molecular level. Proteins, DNA and RNA make up only a small part of any given cell and many assays require significant amounts of these molecules for study.

One approach to the molecular study of disease is to examine DNA of the affected individual. The ability to identify specific pieces of DNA, both in cells and after purification, with nucleic acid probes provides a powerful tool. In addition, cloning and sequencing of DNA allows even minute genetic changes to be accurately identified. One cannot directly ascertain, however, what effects genetic changes have on the expression of a particular disease phenotype. This requires examination of mRNA or protein products relating to the DNA sequence in question.

Alternatively, measuring protein expression and function allows assessment of the impact of these molecules on disease. But direct study of proteins can be problematic. Purification of proteins prior to study in vitro can result in loss of protein sample and cause changes in protein structure and function when compared to that seen in living cells. For example, antibodies, which are used to study proteins, are highly dependent upon protein structure. This structure may be lost during treatment required to make it accessible to the antibody. In addition, proteins are subject to destruction by hardy enzymes called proteases. The presence of proteases may prevent intact purification of proteins or may simply destroy the activity of protein once purified. Finally, unlike DNA, the ability to reproduce native proteins in vitro is exceedingly limited.

Examination of mRNA, in contrast to the study of DNA and proteins, provides information on gene expression while permitting the use of powerful nucleic acid manipulations. However, working with mRNA also presents major difficulties. First, RNA is subject to cleavage by highly active enzymes called RNAses. These enzymes are ubiquitous, nearly impossible to remove from samples, and highly resistant to inactivation. Second, RNA's cannot be cloned and amplified in the same manner as DNA because they are found in single-stranded form. Thus, in hybridization studies one is forced to work with the quantities present in available cells. Yet some mRNA levels, like those of type IV collagen, are so low as to not be detectable by in situ hybridization. Laurie et al. (1989).

The availability of the retroviral enzyme, reverse transcriptase, has made study of RNA's much less difficult. Through reverse transcription, mRNA's can be converted into complementary DNA (cDNA) homologs which can be manipulated with greater ease. cDNA's may also be subjected to PCR, described more fully below, allowing for their rapid amplification. Moriyama et al. (1990).

Reverse transcriptase requires both a template and a free nucleic acid 3'-terminus to begin transcription. mRNA provides the template. While any nucleotide sequence complementary to the mRNA may provide the 3'-terminus, many times the coding sequence of the RNA is not known. Fortuitously, the poly-A tail (a string of deoxyadenosine residues found on most mRNA's which confers stability on the molecule) provides a ubiquitous sequence which can be used to hybridize with a poly-T (deoxythymidine) oligonucleotide. This poly-T molecule "primes" the reverse transcription and, hence, is referred to as a primer. Alternatively, random primers may be used to provide the necessary 3'-terminus. After hybridization and synthesis of the complementary strand and alkali treatment of the RNA/DNA hybrid to degrade the RNA, reverse transcriptase can use the remaining hairpin-loop structure at the 3'-end of the single-stranded DNA as a primer for the complementary DNA strand. Subsequent treatment with S1 nuclease cleaves the hairpin and creates a normal double-stranded DNA molecule.

While reverse transcription is a valuable technique, it cannot overcome the inherent problem of low levels of many mRNA's and, hence, of corresponding cDNA's. Until 1986, the only method for the amplification of cDNA's was by cloning. While this approach can be used, it involves considerable effort, is time-consuming, and not unviversally successful. Moreover, it is often unnecessary since not all assays require permanent retention of a copy of the target DNA.

Polymerase chain reaction has revolutionized molecular biology in the relatively short time it has been available as an experimental tool. This process allows minute amounts of nucleic acids to be amplified by more than one million-fold, so long as some part of the sequence to be amplified, usually 15 to 20 nucleotides in length, is known. Peten et al., *Am. J. Physiol.*, in press (1992). Yet this process can be performed in minutes, unlike the laborious efforts involved in cloning of DNA. It is most useful where, as is the case with collagen message cDNA's, the amount of target nucleic acid is particularly low.

A general strategy, in accordance with the present invention, is to create oligonucleotide sequences which are complementary to a double-stranded nucleic acid to be amplified. One primer is generated which hybridizes to the "plus" or "coding" strand of nucleic acid. A second primer is made which hybridizes to the "minus" or "non-coding" strand. The second primer must also be located "3'" to or "downstream" of the first. After repeated rounds of hybridization, extension of the oligonucleotides with a modified DNA polymerase, denaturation, and rehybridization, the sequences located between the two primers are amplified.

The present invention is conducted in a manner so as to exploit further the power of PCR technology. Use of a competing DNA fragment in PCR provides a reliable and reproducible method for quantitation of the amount of target DNA in the sample. Here, the competing fragment is a mutated version of the DNA to be amplified containing an engineered restriction endonuclease site. Digestion of the PCR products with the appropriate enzyme allows the total amplified DNA to be characterized as having originated either from the target or competing mutant DNA segments. Comparison of the relative amounts of these two populations allows for a determination of the starting amount of the target sequence.

Two other reports have used tissue biopsy coupled with the advanced molecular biologic techniques described above, to search for disease mechanisms. Cerutti, et al., European patent application No. 0 461 496 A1, describe a method for the quantitative determination of DNA sequences containing mutationally-eliminated restriction sites. They suggest that this approach would be successful using tissue explants, e.g., biopsy samples or blood cell samples. Their approach does not target distinct organizational elements of the subject tissue, nor does it attempt to examine expression of a disease phenotype at a molecular level. Cao et al., *AIDS* 6:65–70 (1992), report using liver biopsies to examine HIV DNA levels by PCR and mRNA levels by in situ hybridization. PCR was performed on extracted DNA without regard to particular subsegments of biopsied tissue. Moreover, in situ studies, while quite useful in examining intact tissue structures, are limited in that quantitative analyses are not possible.

In addition to providing the physician with early notice of disease, the diagnosis achieved by the present invention will provide information on the progression of fibrotic disease not formerly within the reach of the physician. First, by determining the degree of fibrosis that exists in the patient, from minor to severe, it may be possible for the physician to tailor treatment for the specific stage of the illness. For example, it may turn out that treatments effective at limiting end-stage fibrosis are ineffective or even harmful to tissue that is only mildy affected. By the same measure, therapy directed at reversing the early stages of fibrosis may not be helpful in treating a severly fibrotic tissue.

Second, the present invention will provide more specific information on the make-up of the fibrotic lesion. This information will generally fall into two categories. While only two collagens (Types I and IV) have been demonstrated as components of the fibrotic lesion, other collagens are known to be important in normal scar formation. Therefore, it is important to determine which collagens, or other as of yet undefined molecules, are present in a particular lesion. It is also possible that different collagens may be involved at different stages or different kinds of fibrotic disease. Thus, knowing the presence or absence of certain collagens and the relative amount of these molecules in the fibrotic lesion may prove important. This information is also likely to have a bearing on the nature and duration of therapy.

Finally, the ability to test a particular patient over an extended period of time permits the physician to obtain a dynamic view of the disease process. Essentially, the physician instituting therapy asks 1) whether the patient is responding, 2) whether the dosage is appropriate, and 3) when may the therapy be terminated. The present invention provides the physician, for the first time, a way of answering these questions. Therefore, not only does the physician gain the opportunity for early intervention, but he or she may more effectively apply treatment once the disease state has been uncovered.

The following examples are meant to be illustrative only and should not be construed as limiting the scope of the invention.

EXAMPLE 1
Subjects

Murine. Kidney tissue was obtained from 5–24 wk B6xSJL F1 male and female mice weighing from 11–30 gm.

Human. Kidney tissue was obtained from nine patients undergoing nephrectomy for renal cancer and from one patient undergoing open biopsy for nephrotic syndrome and severe renal failure of unknown duration.

EXAMPLE 2
Biopsy

Murine. After anesthesia with Avertin (12 µl IP 1:80 solution/g of body weight), the mice were killed by decapitation. The dissection was carried out as described by Moriyama et al. (1990), using a microdissecting microscope (Wild, Heerbrugg, Switzerland). The kidney was flushed with 3 ml of dissection solution A (4° C.; 135 mM NaCl; 1 mM $Na_2HPO_4$; 1.2 mM $Na_2SO_4$; 1.2 mM $MgSO_4$; 5 Mm KCl; 2 mM $CaCl_2$; 5.5 mM glucose; and 5 mM Hepes, pH7.4) and then with 3 ml of the same solution containing 1 mg/ml collagenase (Type I, 300 units/mg, Sigma Chemicals, St Louis, Mo.) and 1 mg/ml bovine serum albumin (molecular biology grade, Boehringer Mannheim, Indianapolis, Ind.). A small, superficial cortical fragment was incubated at 37° C. x35 min in the collagenase solution in the presence of $O_2$.

Human. A small piece of cortex (approximately 10 mm³), far removed from the renal tumor for nephrectomy specimes, was resected with a sterile scalpel blade and placed in a 5 ml solution A and 10 mM vanadyl ribonucleoside complex (VRC) (Life Technologies Gaithersburg, Md.), a particulate ribonucleoside inhibitor, at 4° C.

EXAMPLE 3
Microdissection

Murine. The cortical fragment was transferred to a microdissecting dish cooled to 4° C. and glomeruli were separated from tubules and afferent and efferent arterioles in buffer containing 10 mM VRC.

Human. The cortical fragments were placed at 4° C. in a particulate RNAse inhibitor solution of VRC. The fragments were transferred to a microdissecting dish cooled at 4° C. and glomeruli were separated from tubules and arterioles in the same RNase inhibitor solution.

EXAMPLE 4
Tissue Preparation

Murine. The isolated glomeruli were washed free of tissue debris and VRC in a second dish containing the original dissection solution at 4° C., and transferred to a siliconized PCR tube containing 10 µl of the dissection solution with 5 mM dithiothreitol (DTT) and 1.2 unit/µl of human placental RNase inhibitor (Boehringer Mannheim,). The tubes, containing single or pooled glomeruli, were briefly centrifuged at 15,000 RPM at room temperature to pellet the glomeruli (FIG. 1).

The addition of 1.2 units/µl of placental RNase inhibitor to the final perfusion solution and to the collagenase solution led to better RNA preservation within the glomerular interstices than could be obtained by immersion of the glomeruli in RNase inhibitors only, as previously described (25).

Human. Groups of five glomeruli were washed free of tissue debris and VRC by transferring them to a second dish containing chilled solution A without VRC, and then placed in a PCR tube containing 10 µl of solution A supplemented with human placental RNAse inhibitor, 1.2 units/µl, and 5 mM dithiothreitol (DTT) on ice. The tubes were briefly centrifuged at 15,000 RPM. The supernatant was removed and the glomeruli were permeabilized in a 20 µl solution containing 0.9 percent Triton X-100 (vol./vol.), 1.2 U/µl of RNase inhibitor, 2.25 mM DTT.

EXAMPLE 5
Reverse Transcription

The RNAzol method (Cinna/Biotecx, Laboratories International Inc., Friendswood, Tex.) of RNA extraction was used with tRNA added as a carrier. Immediately before reverse-transcription the RNase inhibitor solution was removed from the PCR tubes and replaced with 9 ml of 2% Triton X-100 containing 1.2 unit/µl of RNase inhibitor and 5 mM DTT. A cDNA synthesis kit (Boehringer Mannheim)

was used. Oligo dT (15 mers) or random primers were used to prime the reverse-transcription for subsequent mRNA amplification. The reaction mixture was incubated for 60 min at 42° C., then stopped by cooling at 4° C. ×10 min, and heat-treated at 90° C. for 7 min to inactivate the reverse transcriptase enzyme. Samples were stored at −70° C. or −20° C. for subsequent manipulations.

Murine. Since the size of glomeruli varied, pools of glomeruli were prepared. Five separate pools of 7 glomeruli per mouse were individually reverse-transcribed, and the cDNA's from 35 glomeruli pooled in a single tube. The cDNA solution was shown to be homogeneous in preliminary experiments, therefore subsequent manipulations were performed using fractions of cDNAs prepared from pooled glomeruli.

Human. Pools of 5 glomeruli were individually reverse transcribed with oligo dT, and ten separate pools were combined to lessen errors due to variations in glomerular size. Schmitz, et al., *Diab.* 37:38–43 (1988). Since the cDNA solution was found to be homogeneous in preliminary experiments, subsequent manipulations were performed using fractions of cDNA prepared from pooled glomeruli.

EXAMPLE 6

Primer Production

Murine. Primers for reverse transcription, 22–24 mers, were synthesized on a PCRMate (Applied Biosystems, Foster City, Calif.), purified by affinity column elution, and kept at −20° C. in water. The mouse α2IV collagen primers were designed in the 3'-untranslated region (UTR) described by Saus et al. in *J. Biol. Chem.* 264:6318–6324 (1989)). The sense primer corresponded to bp 5562–5584 (SEQ ID NO:1:5'ACT CAT TCC AAC CGT CTG TCA GC 3') and the antisense primer to bp 6100–6123 (SEQ ID NO:2:5'GCA AAT CAT TGA CAG TGG CGT CTA 3'). The mouse α1IV collagen primers were also designed in the 3'-UTR. Muthukumaran et al., *J. Biol. Chem.* 264:6310–6317 (1989). The sense primer encompassed bp 5809–5830 (SEQ ID NO:3:5'TAG GTG TCA GCA ATT AGG CAG G 3') and the antisense bp 6271–6292 (SEQ ID NO:4:5'CGG ACC ACT ATG CTT GAA GTG A 3'). The sizes of the corresponding amplified products were 562 bp for the α2IV collagen primers and 484 bp for α1IV collagen primers, as predicted from the corresponding cDNA sequences.

Two additional antisense oligonucleotides were synthesized to serve as amplification product-specific probes for α2IV collagen spanning bp 5781–5804 (SEQ ID NO:5:5'CCT GCA GTC TTC CTA AAA TGA GGC 3') and for α1IV collagen spanning bp 6172–6193 (SEQ ID NO:6:5'GCA TTT CAC ACC TGA GCA CAC A 3'). Both oligonucleotides localized to a sequence internal to the amplification primers.

Several pairs of primers were tested for each gene. The sense-antisense pair chosen gave a single, intense band of the predicted size.

Human. Sense and antisense primers, designed using the previously published cDNA sequence for human TIMP-1 of Carmichael et al., (1986), were synthesized on a PCR-Mate (Applied Biosystems, Foster City, Calif.). A primer pair was chosen to yield an expected product of 442 base pairs. The sense primer sequence was 5'AAT TCC GAC CTC GTC ATC AGG 3'(SEQ ID NO:7) (bp 181–198), and the antisense primer sequence was 5'ACT GGA AGC CCT TTT CAG AGC 3'(SEQ ID NO:8).

The α2IV collagen primers were designed in the coding region of the NC1 domain in which nucleotide sequences allowed specific amplification of the α2 chain, but no other type IV collagen α chain.

EXAMPLE 7

Competitive PCR

PCR was performed using the GeneAmp DNA Amplification kit (Perkin Elmer Cetus, Norwalk, Conn.). The PCR reaction was conducted as described by Moriyama, et al. (1990), but in a final volume of 50 μl. The final magnesium concentration was 1.5 mM for α1IV and 2.0 mM for α2IV collagen mRNA amplification. An initial reaction was conducted to determine the range and relative amounts of mutant and test cDNAs to be added to each tube and the number of PCR cycles required. Competitive PCR assays were set up as follows: (1) a master mix containing that amount of glomerular cDNA representing 1/10th of a glomerulus to be tested and all the PCR kit reagents was prepared and distributed in 45 microliters aliquots into each of 6 PCR tubes (1 additional tube contained all the reagents but no cDNA, as a contamination control); (2) 5 μl of mutant cDNA template in decreasing concentrations were added to the 6 PCR tubes, usually spanning a 1 to 10 attomole range; (3) the PCR cycles were completed, usually in the range of 36.

The thermal cycler (Perkin Elmer Cetus) was programmed so that the first incubation was performed at 94° C. ×3 min, followed by 3236 cycles consisting of the following sequential steps:94° C. ×1 min (denaturation), 60° C. ×1 min (annealing), and 72° C. ×3 min (extension). The final incubation was performed at 72° C. ×7 min. Control tubes omitted the reverse transcriptase enzyme to confirm that relevant genomic DNA was not amplified.

Murine. A quantitative method was established by developing mutated cDNA templates of α1IV and α2IV collagen cDNAs which would compete with test cDNA on an equimolar basis. Gilliland et al., *Proc. Nat'l Acad. Sci. USA* 87:2725–2729 (1990). Briefly, templates for α1IV and α2IV collagen cDNAs were synthesized using PCR site-specific DNA mutagenesis. Ho et al., *Gene* 77:51–59 (1989). The mutated template for α1IV collagen contained a point mutation at bp 6028 (DATP to dCTP) which resulted in a new, unique BclI restriction site. Exposure of amplified mutant template to 10 units of BclI (Life Technologies) at 50° C. ×60 min resulted in complete digestion of the final product into the two expected fragments of 219 and 265 bp. The mutant template for α2IV contained a 83 bp deletion which was introduced into the middle of the cDNA between bp 5833 and 5917, resulting in a mutant cDNA of 479 bp. Following competitive PCR, ten units of BclI were added directly to each tube followed by incubation at 50° C. ×60 minutes for α1IV collagen. Stocks of the mutant cDNAs were synthesized by PCR and purified from a low melting point agarose gel using phenol/ chloroform extraction. The concentration of the purified mutants was determined by comparison with standards (GelMarker I, Research Genetics, Huntsville, Ala.), by densitometric scanning of agarose gels. Serial dilution standards of mutant templates (1000 to 0.0001 attomoles/μl) were stored at −20° C.

Human. The quantitative PCR method for human α2IV collagen was facilitated by the use of a mutant cDNA template. The mutant was synthesized by PCR with a 69 bp deletion in the middle of the α2IV collagen cDNA molecule and purified by phenol/chloroform extraction from a low melting point agarose gel. The concentration of the purified mutants was determined by comparison with standards (GelMarker I, Research Genetics, Huntsville, Ala.), by densitometric scanning of agarose gels. Serial dilution standards of mutant templates (1000 to 0.0001 attomoles/μl) were stored at −20° C.

EXAMPLE 8

Analysis of PCR Products

The entire reaction mix was loaded directly onto a 4% Nusieve:Seakem (3:1) (FMC Bioproducts, Rockland, Me.) agarose gel in a H5 Horizon gel apparatus (Life Technologies, Gaithersburg, Md.) and subjected to electrophoresis. DNA bands were visualized with ethidium bromide staining and UV transillumination. Photographs were taken with positive/negative 55 Polaroid films (Polaroid Corporation, Cambridge, Mass.). Gel negatives were scanned by one-dimensional laser densitometry, for competitive PCR analyses (Shimadzu, Scientific Instruments Inc, Columbia, Md.). The densitometric values of the test and the mutant band(s) were calculated and their ratio for each reaction tube was plotted as a function of the amount of mutant template added. A straight line was drawn by linear regression analysis. The quantity of cDNA in the test sample was calculated to be that amount at which the mutant/test band density ratio was equal to 1. Gilliland et al. (1990). Competitive PCR assays were performed in duplicate or triplicate.

Amplified mutant DNA was distinguished from wild-type cDNA on the basis of differring molecular weights. Where necessary, the amplified cDNA's were treated with the appropriate restriction endonuclease to visualize the differences engineered into the sequences. Upon electrophoresis, mutant DNA's migrated at different rates than the wild-type cDNA's, allowing for determination of the relative amounts of the two DNA populations. Knowledge of the starting concentration of the mutant DNA population allowed for a determination of the starting amount of the wild-type cDNA population.

EXAMPLE 9

Southern Blot Analysis

DNA was transferred to a Nylon membrane (Schleicher and Schuell, Keen, N. H.) with a vacuum blotter (Hoef fer Scientific Instruments, San Francisco, Calif.) and UV-crosslinked (Stratalinker, Stratagene, La Jolla, Calif.). Synthetic oligonucleotide probes described above were end-labeled with $^{32}P$ as described previously. Moriyama, et al., 1990). The amplified products were identified as specific for mouse α1IV or α2IV collagen mRNA and α1IV collagen.

EXAMPLE 10

Statistical Analysis

Murine. Analysis of variance (ANOVA) was used with Bonferroni's post test p corrections for comparisons involving more than two groups, whereas unpaired Student't test was otherwise performed. A p value <0.05 was considered significant. All data are expressed as mean ± standard error of the mean (SEM), unless otherwise specified.

Human. The unpaired Student's t or Mann-Whitney U test was used for comparisons between groups, and Spearman's test was used for ranked correlation. A p value <0.05 was considered significant. All grouped data were expressed as mean ± SEM, unless otherwise specified.

What is claimed is:

1. A diagnostic method for a fibrotic disease comprising the steps of
   (i) obtaining a sample of tissue from an organism by biopsy, wherein said tissue is subject to a fibrosing condition; then
   (ii) isolating by microdissection an intact subsegment of said sample, which subsegment corresponds to a basic organizational structure of said tissue;
   (iii) subjecting mRNA from said subsegment to reverse transcription to obtain cDNA molecules; and thereafter
   (iv) bringing said cDNA molecules into contact with ECM-related PCR primers under conditions such that a ECM-related subpopulation of said cDNA molecules undergoes quantitative amplification, wherein cDNAs of said subpopulation encode protein molecules that are involved in basement membrane-synthetic and -degradative pathways related to said fibrosing condition; and
   (v) analyzing said amplified subpopulation, whereby mRNA levels corresponding to said amplified subpopulation are monitored and a diagnosis is effected therefrom.

2. A diagnostic method according to claim 1, wherein the amount of amplified cDNA molecules is compared with the amount of amplified cDNA molecules of a second organism.

3. A diagnostic method according to claim 1, wherein the amount of amplified cDNA molecules is compared with the amount of amplified cDNA molecules of said organism but generated at an earlier time.

4. A diagnostic method according to claim 2, wherein the obtained tissue is kidney tissue.

5. A diagnostic method according to claim 2, wherein the obtained tissue is lung, liver, skin, muscoskeletal, genitourinary or vascular.

6. A diagnostic method according to claim 4, wherein said organizational structure consists of one or more glomeruli.

7. A diagnostic method according to claim 6, wherein said protein molecules are one or more of basement membrane collagens, interstitial collagens, metalloproteinases, and metalloproteinase inhibitors.

8. A diagnostic method according to claim 5, wherein said protein molecules are one or more of basement membrane collagens, interstitial collagens, metalloproteinases, and metalloproteinase inhibitors.

9. A diagnostic method according to claim 3, wherein the obtained tissue is kidney tissue.

10. A diagnostic method according to claim 3, wherein the obtained tissue is lung, liver, skin, muscoskeletal, genitourinary or vascular.

11. A diagnostic method according to claim 9, wherein said basic organizational structure consists of one or more glomeruli.

12. A diagnostic method according to claim 11, wherein said protein molecules are one or more of basement membrane collagens, interstitial collagens, metalloproteinases, and metalloproteinase inhibitors.

13. A diagnostic method according to claim 10, wherein said protein molecules are one or more of basement membrane collagens, interstitial collagens, metalloproteinases, and metalloproteinase inhibitors.

14. A diagnostic method according to claim 1, wherein said organism is a human.

15. A diagnostic method according to claim 2, wherein said organism is a human.

16. A diagnostic method according to claim 3, wherein said organism is a human.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:1:

ACTCATTCCA ACCGTCTGTC AGC                                              23

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:2:

GCAAATCATT GACAGTGGCG TCTA                                           24

(2) INFORMATION FOR SEQ ID NO:3:

(i) SEQUENCE CHARACTERISTICS:
        (A) LENGTH: 22 base pairs (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:3:

TAGGTGTCAG CAATTAGGCA GG                                            22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:4:

CGGACCACTA TGCTTGAAGT GA                                            22

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:5:

CCTGCAGTCT TCCTAAAATG AGGC                                          24

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:6:

GCATTTCACA CCTGAGCACA CA                                            22

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:7:

AATTCCGACC TCGTCATCAG G                                             21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (iv) ANTI-SENSE: YES (xi) SEQUENCE DESCRIPTION: SEQ ID NO:8:

ACTGGAAGCC CTTTTCAGAG C                                                      21